United States Patent [19]
Houser et al.

[11] Patent Number: 5,989,276
[45] Date of Patent: Nov. 23, 1999

[54] PERCUTANEOUS BYPASS GRAFT AND SECURING SYSTEM

[75] Inventors: Russell A. Houser, Livermore; James G. Whayne, Saratoga; Sid D. Fleischman, Menlo Park, all of Calif.

[73] Assignee: Advanced Bypass Technologies, Inc., Pleasanton, Calif.

[21] Appl. No.: 08/966,003

[22] Filed: Nov. 7, 1997

Related U.S. Application Data

[60] Provisional application No. 60/030,733, Nov. 8, 1996.

[51] Int. Cl.⁶ ................................................. A61B 17/32
[52] U.S. Cl. ............................................ 606/170; 606/139
[58] Field of Search .................................. 606/139, 194, 606/195, 198, 151, 153, 170; 623/1, 3; 604/53

[56] References Cited

U.S. PATENT DOCUMENTS

| | | | |
|---|---|---|---|
| 5,078,736 | 1/1992 | Behl | 623/1 |
| 5,391,156 | 2/1995 | Hildwein | 604/174 |
| 5,405,322 | 4/1995 | Lennox et al. | 604/53 |
| 5,443,497 | 8/1995 | Venbrux | 623/1 |
| 5,628,784 | 5/1997 | Strecker | 623/1 |
| 5,665,117 | 9/1997 | Rhodes | 623/1 |
| 5,695,504 | 12/1997 | Gifford, III et al. | 606/153 |
| 5,697,968 | 12/1997 | Rogers et al. | 623/1 |
| 5,702,418 | 12/1997 | Ravenscroft | 606/198 |
| 5,749,375 | 5/1998 | Maginot | 128/898 |

FOREIGN PATENT DOCUMENTS

| | | | |
|---|---|---|---|
| WO 97/13463 | 4/1997 | WIPO | A61B 17/00 |
| WO 97/13471 | 4/1997 | WIPO | A61M 19/00 |
| WO 97/27893 | 8/1997 | WIPO | A61M 19/00 |
| WO 97/27897 | 8/1997 | WIPO | A61M 29/00 |
| WO 97/27898 | 8/1997 | WIPO | A61M 29/00 |
| WO 98/06356 | 2/1998 | WIPO | A61F 2/06 |
| WO 98/08456 | 3/1998 | WIPO | A61B 19/00 |
| WO 98/19608 | 5/1998 | WIPO | A61B 17/22 |
| WO 98/19618 | 5/1998 | WIPO | A61B 19/00 |
| WO 98/19629 | 5/1998 | WIPO | A61F 2/06 |
| WO 98/19630 | 5/1998 | WIPO | A61F 2/06 |
| WO 98/19631 | 5/1998 | WIPO | A61F 2/06 |
| WO 98/19632 | 5/1998 | WIPO | A61F 2/06 |
| WO 98/19634 | 5/1998 | WIPO | A61F 2/06 |
| WO 98/19732 | 5/1998 | WIPO | A61M 25/01 |

*Primary Examiner*—Michael Buiz
*Assistant Examiner*—(Jackie) Tan-Uyen Ho
*Attorney, Agent, or Firm*—Morrison & Foerster LLP

[57] ABSTRACT

A bypass graft incorporates fixation mechanisms at its opposite ends, for securing these ends to different locations along a blood vessel, or alternatively to different locations wherein one of the locations is a different vessel or an organ defining a cavity. Mechanical fixation features such as collets or grommets can be employed, enhanced by delivery of an electrical current sufficient to heat surrounding tissue to form a thermal bond. A graft deployment system includes a tissue dilator and a needle for perforating tissue, mounted coaxially within the dilator. Intralumenal systems further include a catheter for containing the dilator.

35 Claims, 13 Drawing Sheets

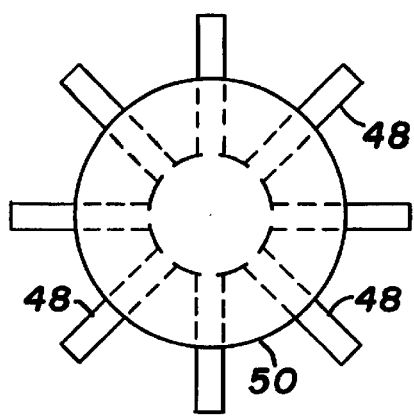
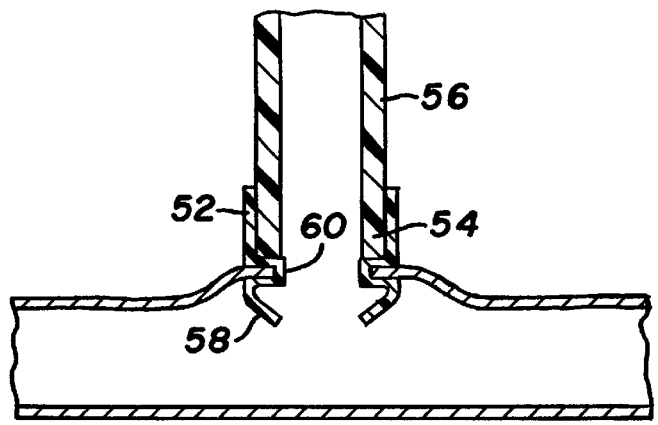
FIG.4          FIG.5
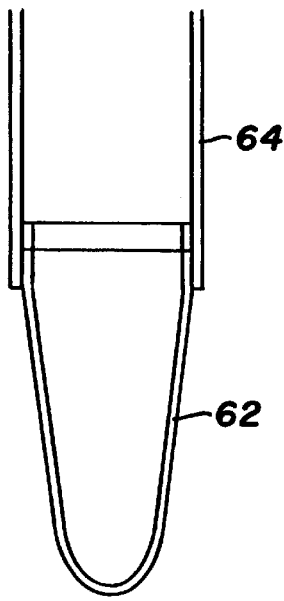
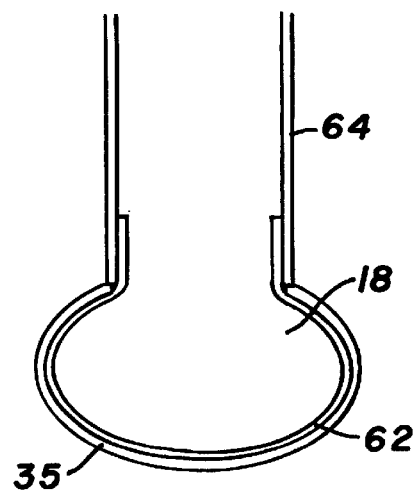
FIG.6          FIG.7
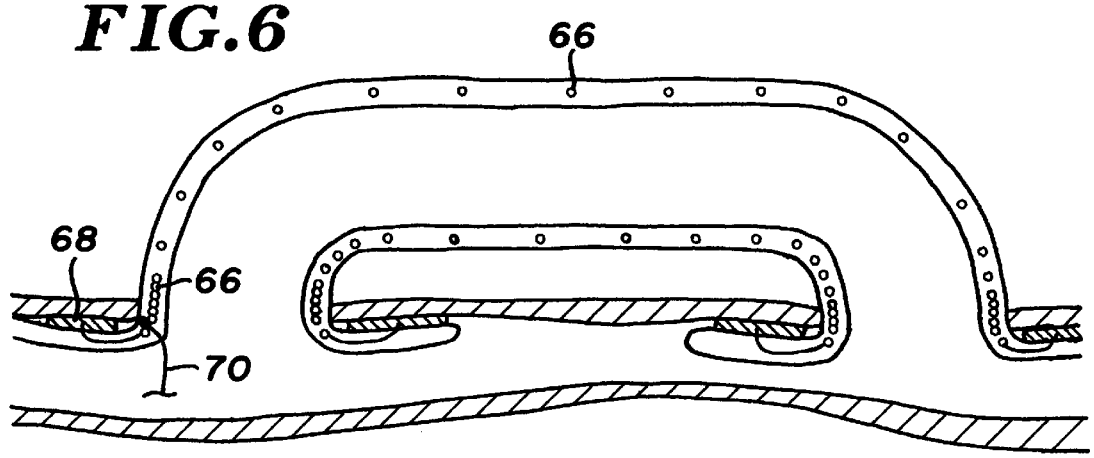
FIG.8

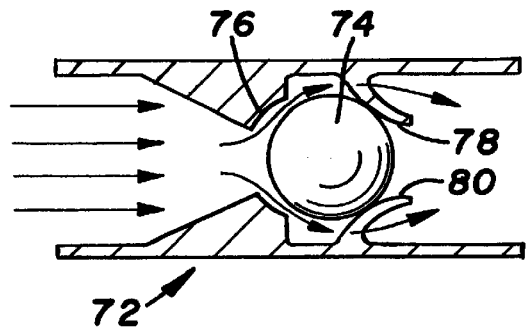
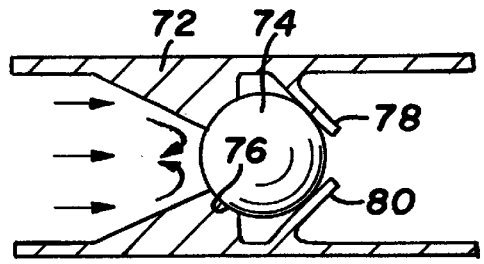
*FIG.9*  *FIG.10*
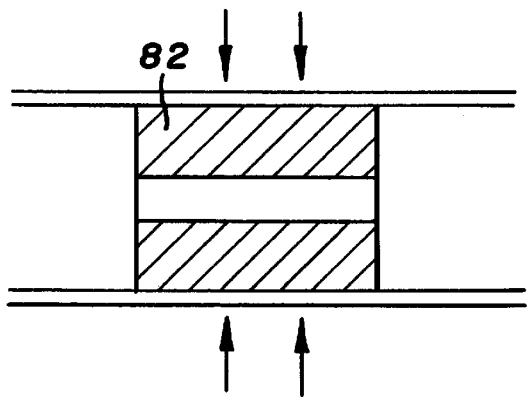
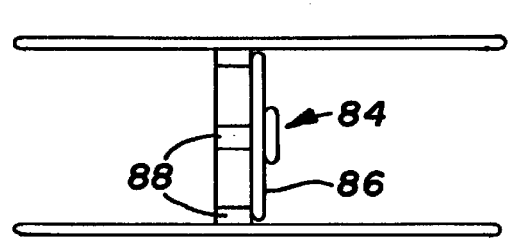
*FIG.11*  *FIG.12*
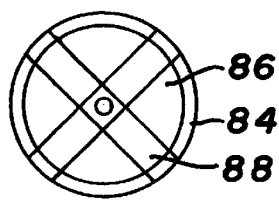
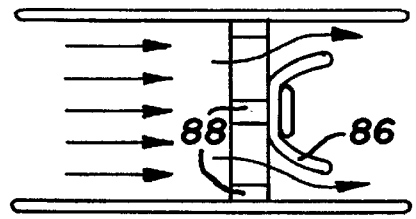
*FIG.13*  *FIG.14*
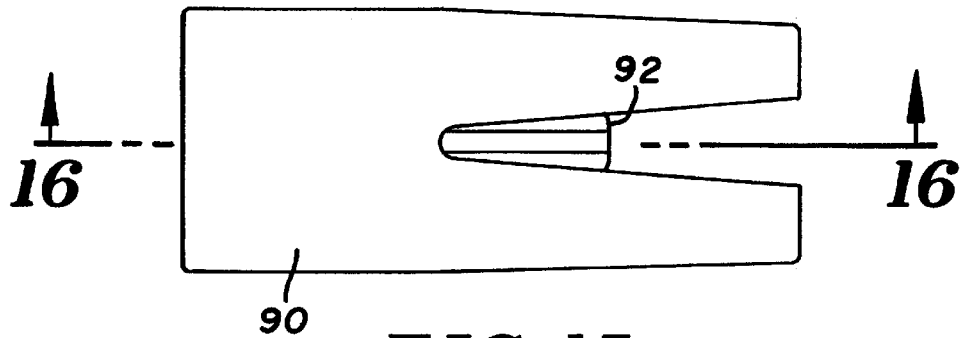
*FIG.15*

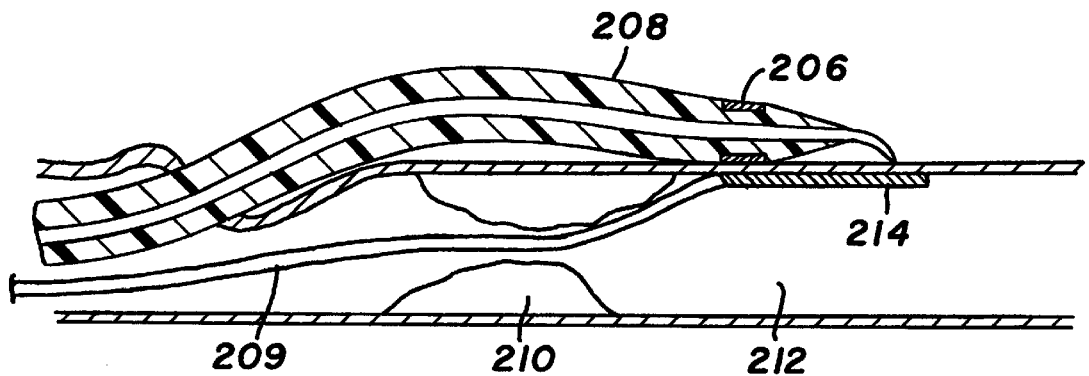
FIG. 25
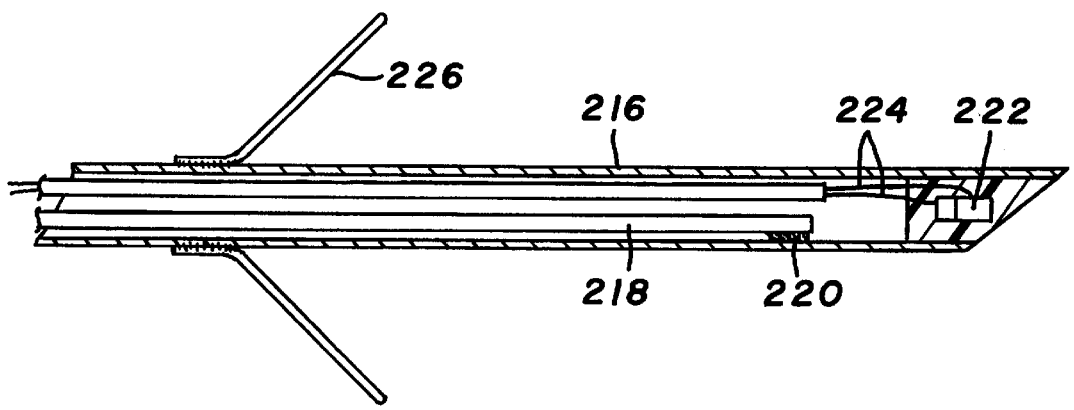
FIG. 26
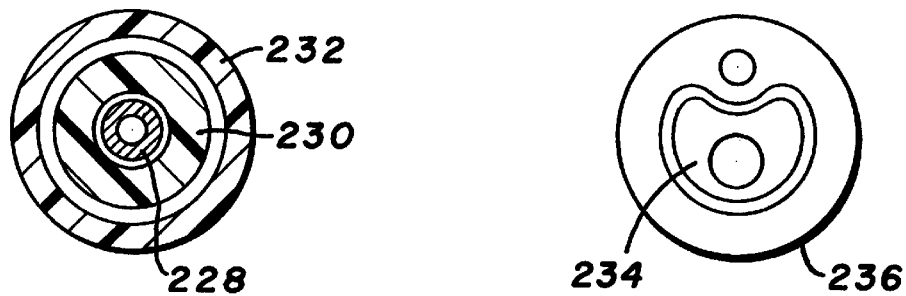
FIG. 27
FIG. 28

PERCUTANEOUS BYPASS GRAFT AND SECURING SYSTEM

This application claims the benefit of priority of Provisional Application No. 60/030,733 entitled Percutaneous Bypass Graft and Securing System, filed Nov. 8, 1996.

BACKGROUND OF THE INVENTION

The present invention relates to grafts implantable to bypass an obstruction or other undesirable condition within a vessel or other tubular organ, and more particularly to systems for deploying such grafts and fixation elements for securing them.

Bypass grafts are particularly useful in treating vascular diseases, but have other applications including treatment of urinary incontinence, infertility, and gastrointestinal defects such as occlusions and ulcers. Stenosed vessels cause ischemia which potentially leads to tissue infarction. Conventional techniques to treat partially occluded vessels include balloon angioplasty, stent deployment, and surgery to attach a graft to bypass the stenosed lesion. Surgical implantation of a bypass graft typically requires performing a thoracotomy, placing the patient on a cardiopulmonary bypass system, and using cardioplegia to induce cardiac arrest. This permits a suturing of the graft between cardiac vessels without the risk of excess blood loss or the need to accommodate motion of the heart. Less invasive attempts at positioning bypass grafts involve a thoracostomy to produce a conduit to the stenosed lesion. This approach uses endoscopic visualization to position the graft. The delivery for such graft requires modified surgical instruments (e.g., clamps, scissors, scalpels, etc.) and further involves ports inserted through small (approximately one inch) incisions to provide access into the thoracic cavity.

There remains a need for a minimally invasive technique for deploying and securing a bypass graft, and for a fixation means for more reliably securing a graft without the need to suture the graft.

Accordingly, it is an object of the present invention to provide a system for translumenal deployment of a bypass graft.

Another object is to provide a more effective fixation means for securing a deployed bypass graft.

A further object is to provide a system for bypass graft deployment, in which features incorporated within the graft reduce the time and difficulty of deployment.

Yet another object is to provide an improved process for deploying and securing grafts along body lumens to bypass obstructions and other undesirable features within the lumens.

SUMMARY OF THE INVENTION

To achieve these and other objects, there is provided a body implantable graft. The graft includes a tubular graft wall having opposite first and second open ends. The graft defines a fluid flow lumen between these ends. The tubular graft is adapted for a selected placement with the first end at a first location in body tissue and the second end at a second location in body tissue, to provide a fluid flow path between the first and second locations to bypass an obstruction between those locations. The graft also includes a graft fixation mechanism operable to heat the graft wall at least near the first end following placement, to thermally secure the graft wall and adjacent tissue.

The preferred fixation apparatus is an electrically conductive heating element mounted to the graft wall near the first end. The element can be annular, and may incorporate a feature to mechanically secure the graft, e.g., a collet or a grommet.

In similar fashion an electrically conductive heating element or other fixation apparatus can be used to secure the second end of the graft at the second location. The heating elements can be coupled to an RF power source and used in conjunction with an indifferent electrode, to secure the graft by ohmic heating.

Another aspect of the invention is a system for deploying a bypass graft. The system includes an elongate and flexible carrier having a proximal end and a distal end. The carrier is insertable by the distal end for intralumenal movement toward a selected site along a body lumen while the proximal end remains outside the body. A tissue perforating mechanism, near the distal end of the carrier, is positionable at a first location near the selected site, and operable from the proximal end of the carrier to form a first opening through tissue at the first location. Further, the mechanism is positionable at a second location near the selected site and operable to form a second opening through tissue at the second location. An elongate graft guide, supported by the carrier and disposed near the distal end, is movable into a guiding position in which the guide extends from the first location through the first opening to the second location and through the second opening. The system further includes a tubular graft adapted to be mounted to the carrier for movement along the carrier. A graft controller is operable to move the graft distally along the carrier toward the graft guide, and then distally along the graft guide when the guide is in the guiding position, to a bypass location in which the graft extends from the first location to the second location and also extends through the first and second openings.

The preferred carrier is a catheter having a catheter lumen. An elongate dilator is contained slideably within the lumen, and has a tapered distal tip. An elongate needle is slideably contained within the dilator.

According to one embodiment, the dilator provides the graft guide, while the tissue perforating mechanism includes the needle and the distal tip of the dilator.

According to another embodiment, a distal end region of the catheter provides the graft guide. The dilator and needle are used to perforate and dilate tissue to form the first and second openings. The dilator is not used to guide the graft, but is used to guide the catheter, particularly the distal end region which in turn is used for positioning the graft after withdrawal of the dilator.

According to another aspect of the present invention, an alternative system is provided for implanting a bypass graft without the need for a catheter. This system includes a tissue dilating member having at its distal end a tissue dilating tip converging in the distal direction. A tissue puncturing tool is supported within the dilating member and extends in the distal direction from the dilating tip. The tool is adapted to puncture or perforate a tissue wall to form an orifice enlargeable by the dilating tip. The system includes a graft with a substantially fluid impervious graft wall. First, second and third openings are formed through the graft wall at first, second and third spaced-apart regions of the wall, respectively. The graft is adapted for a removable mounting on the dilating member in which the dilating member extends through the first and third openings, with the first opening near the dilating tip and the third opening proximally of the first opening. This enables use of the dilating member to insert the first region of the graft wall into a first orifice in the tissue wall, for fixation of the first region in the first orifice. The graft further is slideable relative to the dilating member to permit a proximal withdrawal of the dilating member from the first region after its fixation, and further to allow an insertion of the dilating member into the second opening for securing the second region of the graft wall within a second orifice in the tissue wall. As a result, the graft provides a fluid flow conduit between the first orifice and the second orifice. A closure mechanism is provided for closing the third opening, following withdrawal of the dilating member from the graft, after the first and second regions have been secured.

Another aspect of the present invention is a process for translumenally deploying a bypass graft, including the following steps:

a. advancing an elongate catheter intralumenally toward a selected site along a body lumen;

b. with a distal end of the catheter near the selected site, using a tissue perforating mechanism mounted near a distal end of the catheter to form a first opening through a tissue wall defining the body lumen;

c. advancing tissue perforating mechanism through the first opening, and then to a selected location spaced apart from the first opening, then using the mechanism to form a second opening through tissue at the selected location;

d. advancing a graft guide through the first opening, distally to the selected location, then through the second opening;

e. with the graft guide so positioned, advancing a tubular graft along the guide to a bypass location in which the graft extends from the first opening to the second opening and through the first and second openings, thus to form a bypass conduit in fluid communication with the body lumen; and f. while maintaining the graft in the bypass location, proximally withdrawing the catheter, the tissue perforation mechanism and the graft guide.

Thus, in accordance with the present invention, bypass grafts are deployed more easily using techniques that are considerably less invasive, and upon deployment are more reliably secured.

IN THE DRAWINGS

For a further understanding of the above and other features and advantages, reference is made to the following detailed description and to the drawings, in which:

FIGS. 2–7 illustrate alternative couplings for mechanically fixing the opposite ends of bypass grafts;

FIG. 8 illustrates an alternative embodiment graft incorporating structural supports;

FIGS. 9–16 illustrate alternative embodiment grafts incorporating valves;

FIGS. 22–25 illustrate alternative embodiment dilators;

FIG. 26 illustrates a tissue perforating needle used with the dilators of the various deployment systems;

FIG. 27 is a sectional view of a needle and dilator contained within a catheter;

FIG. 28 illustrates an alternative embodiment dilator within a catheter;

Figure 31A:
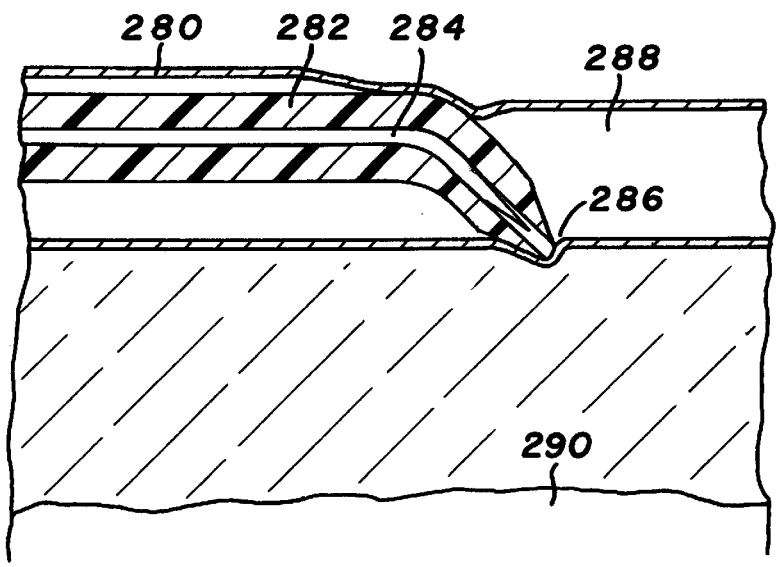
Figure 31B:
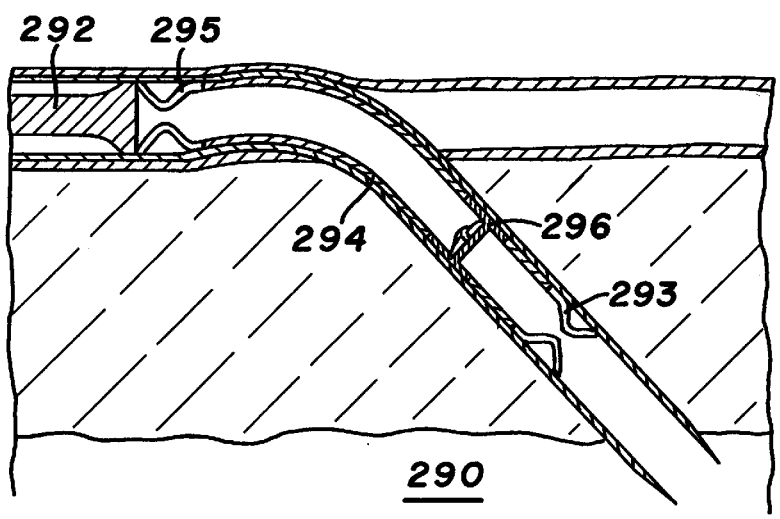
Figure 31C:
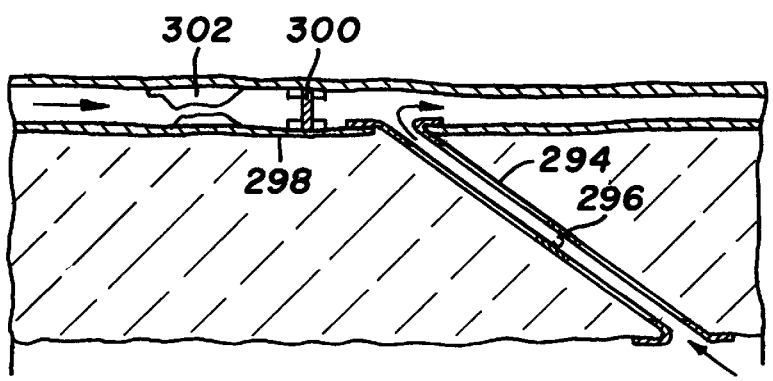
Figure 32:
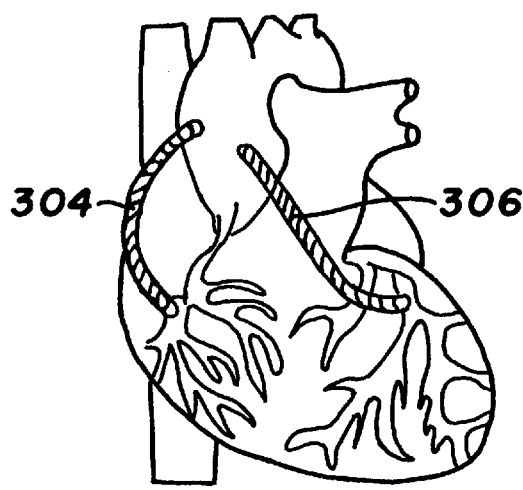

FIGS. 29a–h illustrate a series of steps of a percutaneous deployment and fixation of a bypass graft according to the present invention;

FIGS. 30a–d illustrate an alternative deployment and fixation procedure;

FIGS. 31a–c illustrate a further alternative deployment and fixation;

FIG. 32 shows several bypass grafts secured to the heart; and

Figure 33:
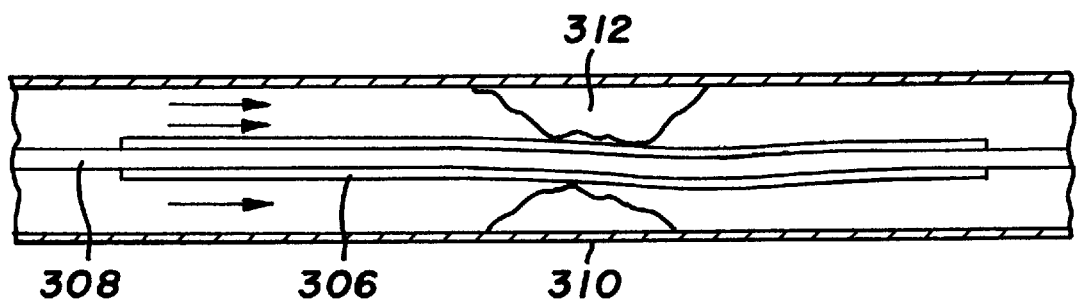
Figure 34:
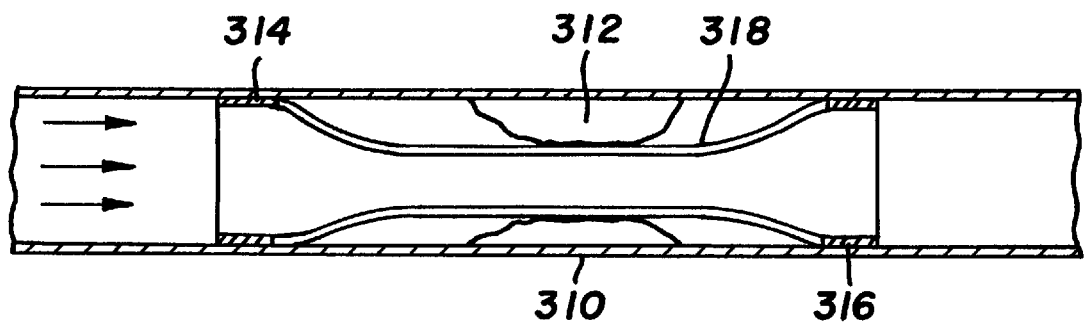

FIGS. 33 and 34 illustrate an alternative graft secured within a vessel.

DETAILED DESCRIPTION OF THE PREFERRED EMBODIMENTS

Figure 1:
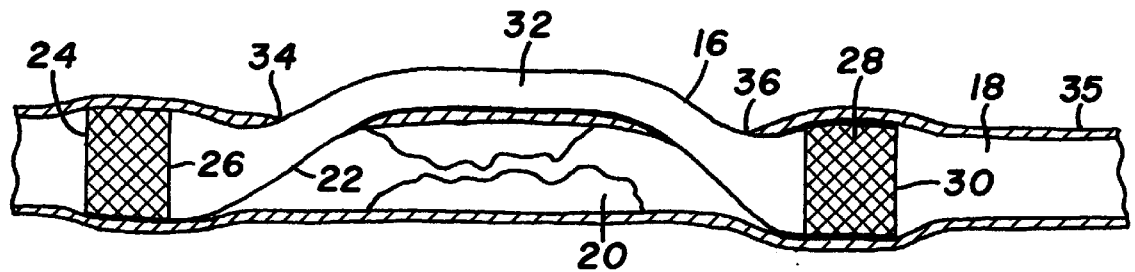
FIG. 1 is a side view, partially in section, of a bypass graft constructed according to the present invention and secured within a vessel.

Turning now to the drawings, there is shown in FIG. 1 a bypass graft 16 secured within a blood vessel 18, in a manner to bypass a lesion 20 within the vessel. Bypass graft 16 has a tubular wall 22 formed of a graft material, e.g., a polymer such as PTFE, urethane, polyimide, nylon, silicone, or polyethylene. The polymer may be extruded, blow molded, or dipped, and formed either directly into a tubing, or formed first as a sheet having opposed ends or edges bonded together to provide the tubular configuration. The edge bond can be formed by a variety of methods including ultrasonic welding, thermal bonding, sewing, adhesives, or with radio frequency (RF) energy. Alternatively, the graft can be a saphenous vein or other vessel from the patient.

At its proximal end 24, bypass graft 16 incorporates a radially expandable stent 26. The graft incorporates a similar stent 28 at its distal end region 30. Once graft 16 is deployed, the stents are radially expanded using a dilatation balloon or a mechanism such as those described in co-pending patent application Ser. No. 08/911,838 entitled "Mechanical Stent and Graft Delivery System," filed Aug. 15, 1997. Alternatively, the graft end regions can have a self-expanding structure, as described in co-pending patent application Ser. No. 08/932,566 entitled "Radially Expanding Prostheses and Systems for Their Deployment," filed Sep. 19, 1997. In either event, each stent and its surrounding graft material are expanded into intimate contact with wall 22 of vessel 18, thus to secure the graft.

As seen in FIG. 1, graft 16 bypasses lesion 20, in the sense that a medial region 32 of the graft is disposed outside of vessel 18. For convenience, the graft can be considered to exit the vessel at an exit opening or orifice 34 through vessel wall 35, and re-enter the vessel at a return opening or orifice 36.

Figure 2:
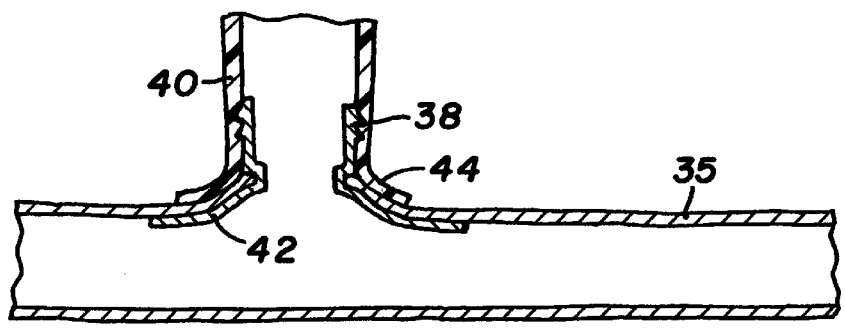

Tubular bypass grafts such as graft 16 can be secured within vessel walls or to other tissue by a variety of fixation mechanisms other than expandable stents. For example, FIG. 2 illustrates an annular collet 38 attached to one end of a graft 40. The collet may be laminated or bonded to the graft, and is pre-formed to have a segment 42 extending radially beyond the graft. Segment 42 also is collapsible into a low profile to facilitate introduction through vasculature and deployment through the vessel wall. When released, the collet assumes the pre-formed configuration as shown. A portion 44 of the graft may extend along collet segment 42 to secure the vessel wall between the graft material and the collet and provide additional support for attaching the graft to the vessel.

Figure 3:
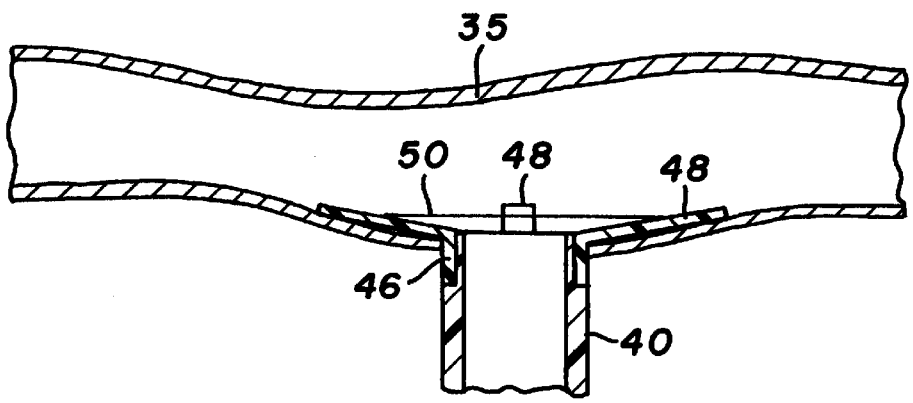

FIGS. 3 and 4 illustrate a collet 46 in which the radially extending collet segment is comprised of eight radially extended collet members 48. A membrane 50 may be joined to the collet members to prevent fluid flow through the tissue wall puncture site.

FIG. 5 shows a further alternative support mechanism in the form of an annular grommet 52 secured to end region 54 of a graft 56. The grommet incorporates a convergence 58 to facilitate insertion through a vessel wall orifice, and a necked down feature 60 to capture the vessel wall immediately about the orifice.

As yet another mechanical fixation alternative, flexible bands 62 can be fixed to an end region of a graft 64 as shown in FIGS. 6 and 7. Each band or other flexible member is compressible into the reduced profile shown in FIG. 6 and remains in that profile while constrained, e.g., by a surrounding catheter. When the graft is released from the catheter, band 62 assumes the radially enlarged, more circular profile shown in FIG. 7. Pluralities of such bands can be provided in crossing patterns at the graft ends, if desired.

For increased strength, particularly where a bypass graft is required to exert a radially outward force against a stenosed lesion, a blood vessel wall or other tissue, the graft can incorporate structural support members 66. The support members can be constructed of metal or a polymer having a higher modulus of elasticity than the graft material. As shown in FIG. 8, support members 66 can be distributed throughout the graft, with a greater density at the graft end regions to enhance fixation within openings through tissue. Support members 66 can have elliptical or rectangular profiles that enhance their strength in a selected direction.

If desired, such support members can be used in lieu of stents 26 and 28 for securing graft ends within a vessel. The support members may be laminated in the graft material. Fabrication can involve extruding or dipping an initial graft layer, winding the support members on the layer, then extruding or dipping to form a second layer covering the support members. Alternatively, the separate layers may be bonded together, or support members may be threaded through the graft material.

If desired, thermal bonding may be employed to augment the mechanical fixation and form a more positive fluid seal. More particularly, electrode strips 68 are mounted to the graft near the graft ends, and coupled through wires 70 to an energy source (e.g., an RF generator) which generates a current to heat adjacent tissue. When sufficient energy is supplied to the electrodes, the graft edges are thermally secured to the vessel wall by a coagulation of the tissue to the electrode, or by desiccation of the vessel wall to provide an interference fit between the reduced-diameter vessel and the graft, especially where the graft and support members exert a radial force. This better secures the graft to the vessel wall and prevents leaks at the graft edges. Suitable materials for the electrodes, which are body compatible as well as electrically conductive, are platinum, platinum-iridium, stainless steel, and gold.

Once the graft has been sealed, signal wires 70 are removed from the graft by delivering a D.C. current through the signal wires at an amplitude sufficient to cause a breakdown of the signal wire, e.g., at a reduced-diameter weak point near its associated electrode. Alternatively, the signal wire can be cleaved, or mechanically removed by applying tension to sever the wire at a reduced-diameter neck region.

On occasion, it is desirable or necessary to ensure that flow of blood or other fluids through the graft is un-directional. To this end, a valve may be placed within the graft, preferably along the medial region. FIGS. 9–16 show a variety of graft constructions.

Turning first to FIGS. 9 and 10, a valve 72 includes a valve ball 74 within a surrounding structure that provides a valve seat 76 on one side of the ball, and upper and lower retainers 78 and 80 on the other side of the ball. In FIG. 9, the valve is open and allows flow in the direction of the arrows, around the valve ball and through open spaces between the valve ball and surrounding structure in the area not occupied by the upper and lower retainers.

As shown in FIG. 10, flow in the opposite direction is substantially prevented by a lodging of ball 74 against the valve seat. Further, the valve functions as a pressure relief valve in that the flow from left to right as viewed in the figure must be sufficient to overcome the tendency of retainers 78 and 80 to urge the ball valve against the valve seat.

FIG. 11 shows a valve 82 designed to react to the muscular contraction to restore normal vessel function. Muscular contraction forces the valve ends inward, opening the valve to permit fluid flow. The force required to open the valve may be selected, depending on the material, wall thickness, length, and geometry. A solid valve requires more force than a valve in which material is selectively removed to maintain the valve function yet decrease the required compressive force to open the valve.

FIGS. 12–14 show a one-way valve 84 having a membrane 86 that closes over valve support struts 88 when no external pressure is present. When pressure is applied due to a fluid flow, membrane 86 distends outwardly away from the struts as seen in FIG. 14, permitting the flow of fluids. Fluid flow in the opposite direction (right to left as viewed in FIGS. 12 and 14) is prevented.

Figure 16:
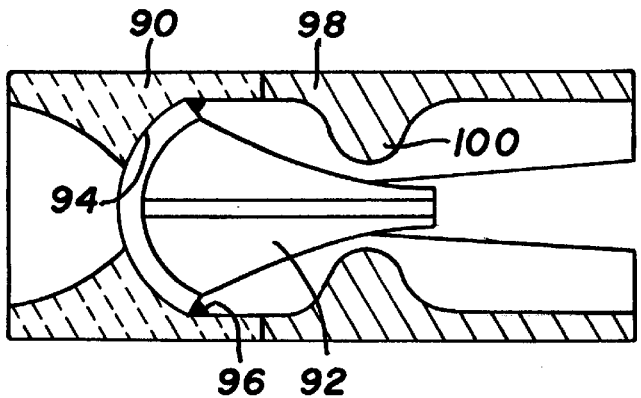

The valves in FIGS. 9–10 and 12–14 act as pressure relief valves, in the sense that they may be tailored to require a selected force to open them, and they remain open only when the applied pressure exceeds the valve resistance. As a result, these valves characteristically remain open for short periods of time. Alternatively, FIGS. 15 and 16 show a pressure relief valve 90 that opens due to pressure exerted on the valve, and remains open until a compressive closure force is applied. Valve 90 includes a plunger 92 movable within a surrounding structure including a valve seat 94 and a knob structure 96 for retaining the valve against the valve seat. The outer structure, which can be the graft itself, includes a flexible section 98 including a protrusion 100 that can be flexed radially inwardly responsive to external pressure.

The knob structure maintains the valve closed until pressure against the valve, i.e., acting from left to right as viewed in FIG. 16, exceeds a selected threshold and opens the valve to allow rightward flow. Even after such pressure subsides, the valve remains open until external, radially inward pressure is applied to compress flexible section 98 of the graft. This moves the plunger leftward, returning it beyond the knob structure against the valve seat, thus closing the valve once again.

Valve 90 is particularly well-suited for treating urinary incontinence. When bladder pressure exceeds the relief valve pressure threshold, the valve is opened to permit the flow of urine. When the bladder pressure is relieved, muscular contractions or other external squeezing flexes section 98 to return plunger 92 to the valve seat, thus closing the valve.

Systems for deploying grafts may require an incision, or alternatively may involve translumenal delivery for a substantially noninvasive procedure. In the latter case, the system must restrain the graft during introduction through sheathes positioned via the Seldinger technique or a surgical cut-down, advancement through the vasculature and into the target vessel. Unwanted perforations of the vessel or other tissue must be avoided. This requires flexibility to follow a guide wire positioned in the target vessel. Further, the system must facilitate easy and accurate deployment of the graft and delivery components. If a partially deployed graft needs to be altered as to location, the system should permit recapture and repositioning. Graft delivery systems may incorporate the capacity to mechanically create intimate contact of the graft with surrounded tissue, especially at the graft ends. This capability is discussed in the aforementioned application Ser. No. 08/911,838 entitled "Mechanical Stent and Graft Delivery System."

Figure 17:
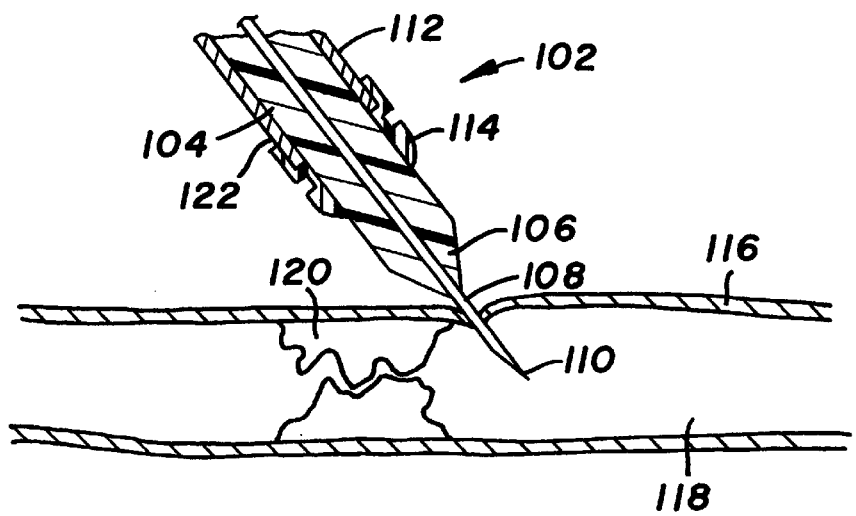
FIGS. 17 and 18 are side sectional views of a bypass graft and system for securing the graft to a vessel wall, in accordance with the present invention.
Figure 18:
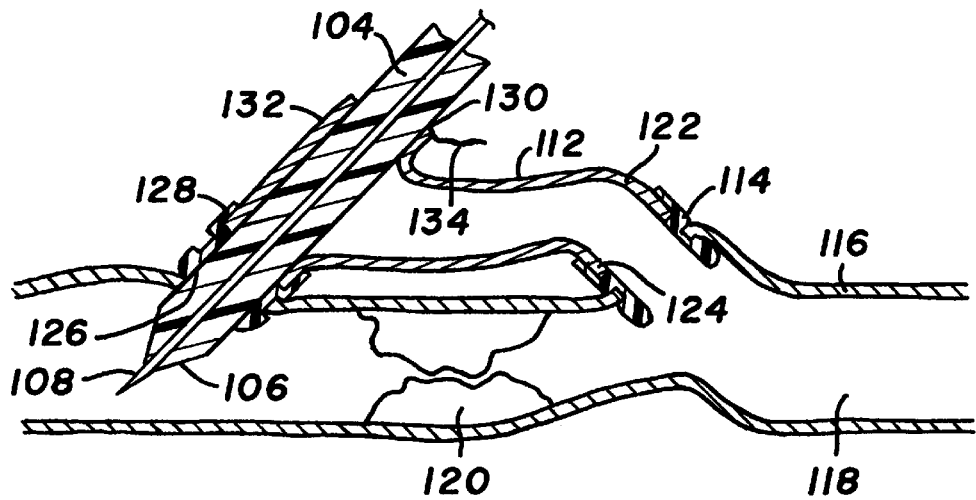

FIGS. 17 and 18 show a bypass graft deployment system 102 that requires an incision. The system includes a dilator 104 having a tapered (distally converging) distal tip 106. A needle 108 is mounted coaxially within the dilator, and has a sharp cutting edge 110 for puncturing or perforating tissue. A bypass graft 112, having a grommet 114 or other suitable fixation mechanism, is supported on and surrounds the dilator.

Use of system 102 requires an incision characteristic of a surgical cut-down, through the dermal layers near the vessel to provide an insertion port. Needle 108, which can be slideably contained within the dilator if desired, is introduced into the insertion port and punctures a wall 116 of a vessel 118 on one side of a stenosed lesion 120. The dilator then is advanced over the needle to enlarge the puncture to provide an orifice for fixation of the graft. At this point, graft 112 is advanced over the dilator sufficiently to position grommet 114 within the orifice. Thus, a first region 122 of the graft is secured, so that an opening 124 of the graft is in fluid communication with vessel 118.

As seen in FIG. 18, graft 112 has two further openings: an opening 126 surrounded by graft material and a second grommet 128; and a more proximally disposed opening 130, where no grommet or other fixation device is provided.

Progress from the view of FIG. 17 to the view of FIG. 18 involves, in part, securing region 122 and grommet 114 as just described. Next, dilator 104 and needle 108 are withdrawn proximally, sufficiently to remove them from region 122. Then, the dilator and needle are distally inserted through opening 126, to become surrounded by grommet 128 and a graft region immediately about opening 126 as shown in FIG. 18. At this point, needle 108 is advanced to puncture tissue wall 116, and dilator 104 is used to enlarge the puncture, to form a second orifice on the opposite side of lesion 120. Then, as shown in FIG. 18, the dilator and graft are advanced sufficiently to position grommet 128 within the orifice.

After grommet 128 is secured, the dilator and needle are withdrawn from opening 126, and further are withdrawn from a region 132 of the graft surrounding opening 130 so that the dilator and needle are completely free of the graft. Then opening 130, which is provided only to allow access of the dilator and needle, is closed to prevent fluid leakage from the graft. One suitable closure mechanism is a pursestring, formed by threading a suture through the graft material in region 132. Other closure mechanisms include staples or adhesives.

In multiple lumen applications, the bypass graft may have four or more openings to accommodate three or more fluid couplings to vasculature or organ cavities.

Figure 19:
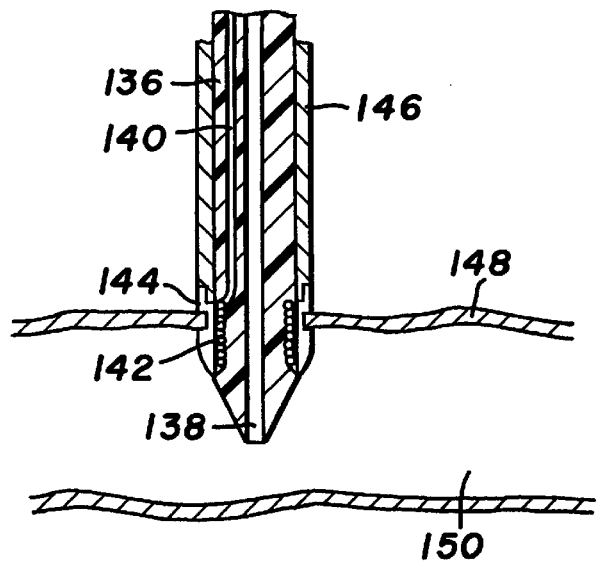
FIGS. 19 and 20 illustrate tissue dilators of alternative embodiment deployment systems employing thermal bonding.

Alternative embodiment deployment systems use different approaches for graft fixation. For example, FIG. 19 shows a dilator 136 with a central lumen 138 for a needle (needle not shown). The dilator also incorporates a lumen 140, through which a signal wire can extend for coupling with a dilator electrode 142. Electrode 142 delivers RF energy to a grommet 144 at the distal end of a graft 146 surrounding the dilator, thus to thermally secure the grommet to a tissue wall 148 of a vessel 150.

Figure 20:
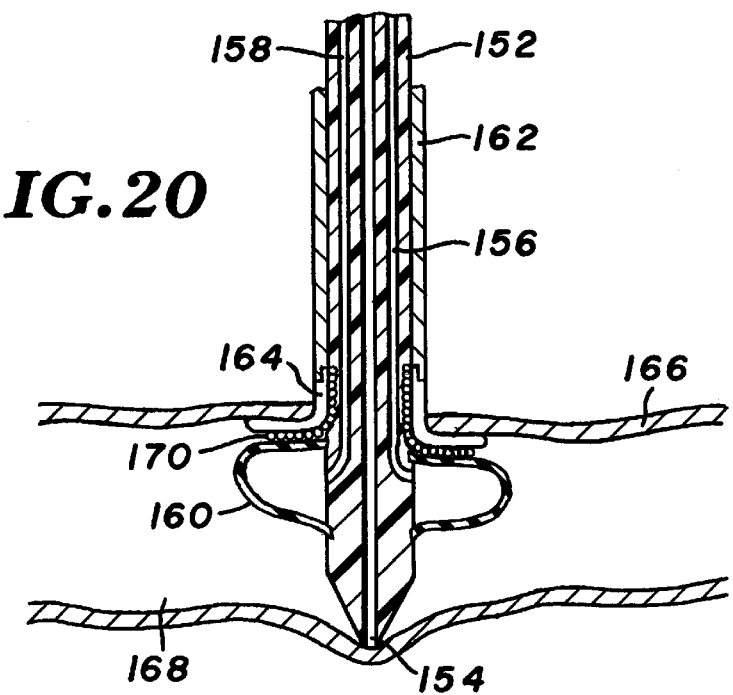

In FIG. 20, a dilator 152 includes, along with a central needle lumen 154, a signal wire lumen 156 and a balloon inflation lumen 158 open to a balloon 160 near the distal end of the dilator. The dilator supports a surrounding graft 162 having a collet 164 at its distal end.

Following insertion of the dilator through wall 166 of vessel 168, balloon 160 is inflated to temporarily secure the dilator, which also bends a portion of collet 164 into the retaining position as shown. An electrode 170, mounted on the exterior of balloon 160, receives a current from a signal wire contained in lumen 156, for thermally bonding collet 164 to the surrounding tissue. After thermal bonding, the balloon is deflated and the dilator withdrawn.

Figure 21:
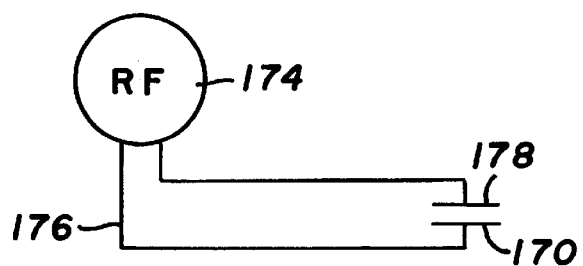
FIG. 21 is a schematic illustration of a circuit for thermal bonding.

FIG. 21 illustrates a schematic circuit for ohmic heating of tissue, usable in conjunction with electrode 170, other dilator supported electrodes, or electrodes mounted directly to a graft as previously described. An RF power generator 174 is coupled to the electrode through a signal wire 176. An indifferent electrode 178, spaced apart from electrode 170 and typically placed on a patient externally, is coupled to the RF generator through a conductor 180. Thus, a current is generated through tissue between electrodes 170 and 178, heating the tissue to form the bond.

Figure 22:
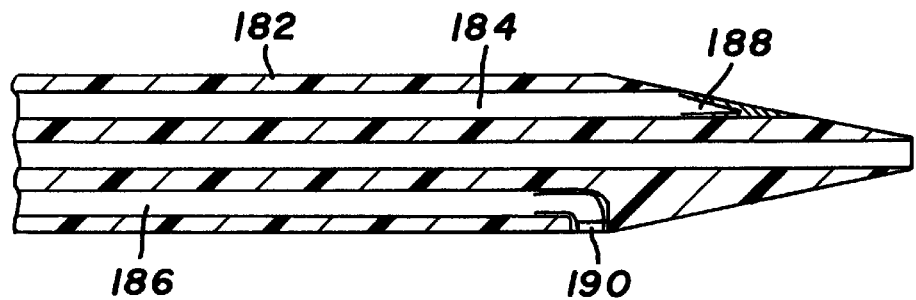
Figure 23:
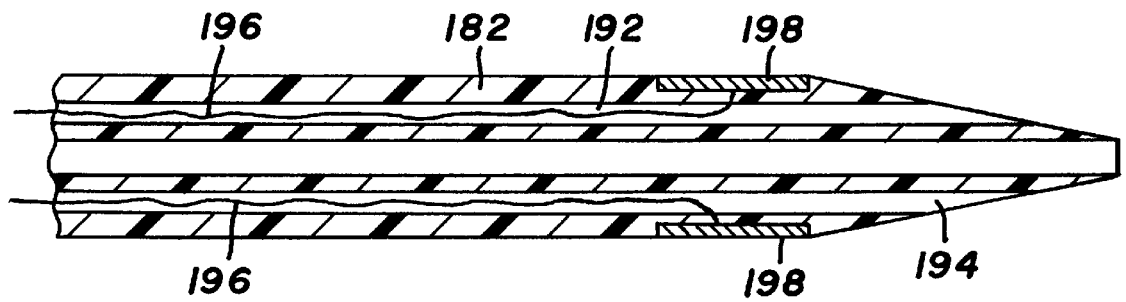

FIGS. 22 and 23 are sectional views of a distal region of a dilator 182, taken at different angles to show different lumens through the dilator. Lumens 184 and 186 in FIG. 22 accommodate signal wires to sensors or transducers 188 and 190 (further discussed below), which can be used to direct placement of the dilator at puncture sites. Sensor 188 is positioned for axial sensing, while a sensor 190 is oriented for lateral sensing. Several sensors 190 can be angularly spaced apart from one another about the dilator circumference. Lumens 192 and 194, shown in FIG. 23, accommodate signal wires 196 to electrodes 198 used for thermal bonding.

Figure 24:
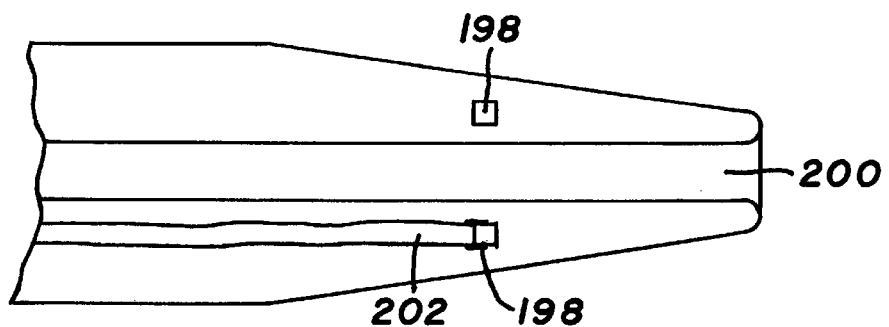

As shown in FIG. 24, a steering mechanism can be incorporated into the dilator to facilitate positioning of the dilator and needle for tissue perforations. In particular, a ring 198 is embedded in the dilator distal tip, surrounding needle lumen 200. A wire 202 is attached to ring 198. By pulling wire 202, the distal tip can be biased downwardly as viewed in the figure.

To further assist positioning, magnets may be incorporated into the dilator near its distal tip, as indicated at 206 for a dilator 208 shown in FIG. 25. Such magnets may be formed of ferrite materials, or alternatively may be formed by winding conductive coils around the dilator to form electromagnets when current is supplied. The dilator magnets are used in conjunction with a guide wire 209 advanced beyond a stenosed lesion 210 within a vessel 212. The guide wire is formed of metal, and to further enhance magnetic attraction may incorporate a magnet 214 of opposite polarity to the dilator magnet. Magnetic positioning facilitates placing bypass grafts through tortuous vessels or over long distances beyond the lesion. Alternatively, known imaging techniques can be used to locate the dilator magnets.

As seen in FIG. 26, a needle also can be provided with steering capability, in particular by forming a hollow needle 216 and securing a wire 218 to a distal portion of a needle through a weld or solder joint 220. A sensor 222 at the needle tip, coupled to wires 224 contained within the needle lumen, can be used to sense a position of the needle tip. A further needle enhancement is a stop 226. When open as shown in FIG. 26, stop 226 limits the degree to which needle 216 can be inserted into tissue, thus preventing excessive, damaging perforations. At the same time, stop 226 is collapsible into a diameter substantially the same as that of the needle when the needle is withdrawn into a dilator.

Intralumenal graft deployment systems also utilize dilators and needles as described, but further incorporate catheters. A suitable arrangement, as shown in FIG. 27, includes a needle 228 surrounded by a dilator 230, which in turn is surrounded by a catheter 232, all components being coaxial and circular in profile.

An alternative arrangement, shown in FIG. 28, incorporates non-circular features into a dilator 234 and a lumen of a catheter 236. The non-circular matching features allow transmittal of torque from catheter 236 to dilator 234, enabling selective rotation of the dilator by rotating the catheter.

FIGS. 29a–29h illustrate progressive steps in a percutaneous, intralumenal deployment of a graft 238, to bypass a lesion in a vessel 240. The system includes a catheter 242 with a lumen 244 containing graft 238, a dilator 246 and a needle 248 within the dilator.

Figure 29A:
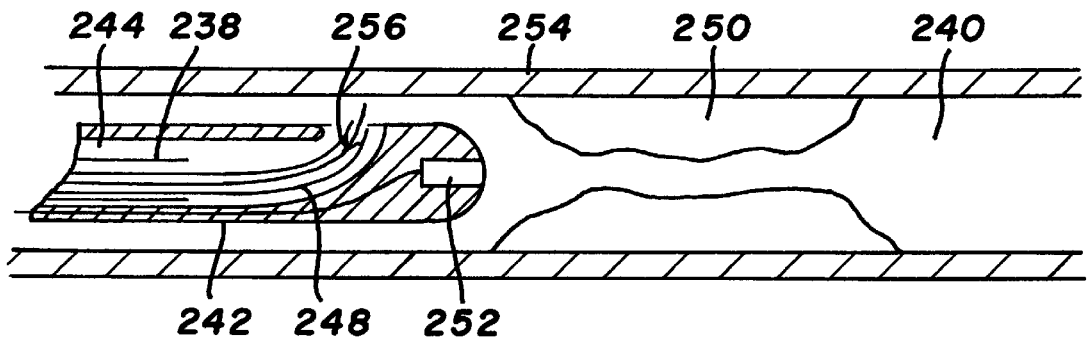

First, the catheter and other components are advanced intralumenally to the proximal side of lesion 250 as shown in FIG. 29a. Sensors 252 facilitate positioning. Such sensors can include ultrasonic transducers of piezoelectric material, infrared transducers, or fiber-optic elements. Alternatively, a radiopaque contrast material may be injected to enhance fluoroscopic visualization.

Figure 29B:
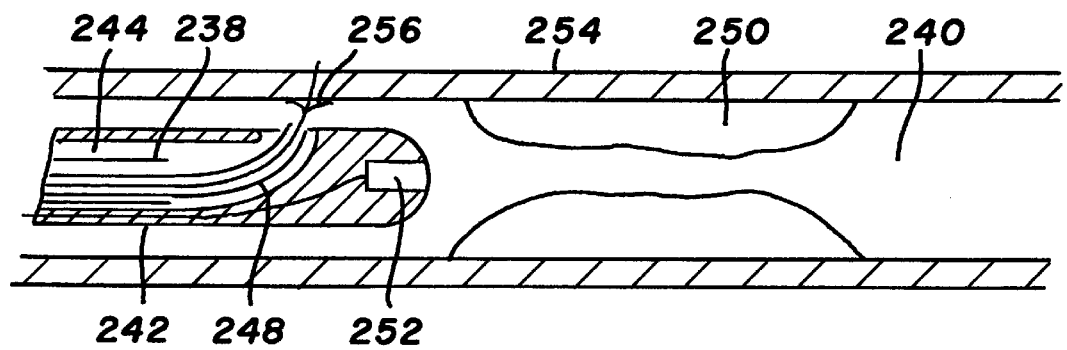
Figure 29C:
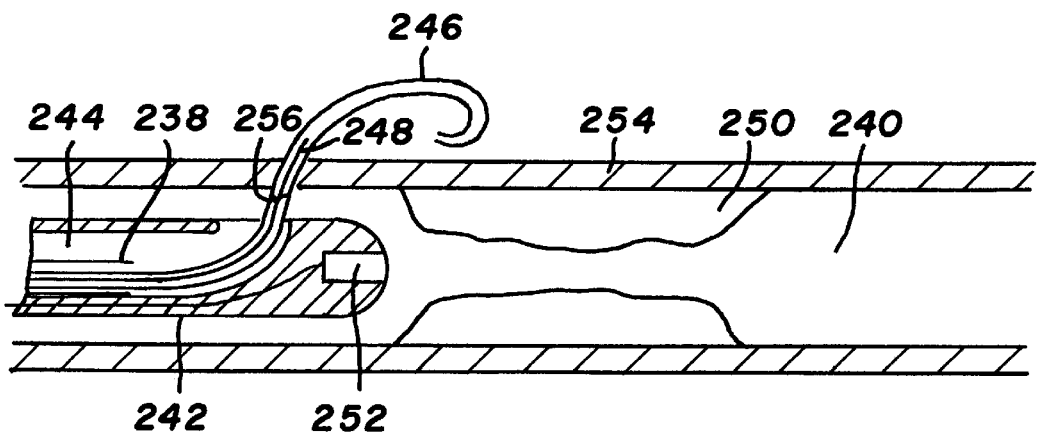

As seen in FIG. 29b, needle 248 is advanced to puncture vessel wall 254. A stop 256 restricts movement of a needle if necessary. Then, dilator 246 is advanced, collapsing stop 256 and enlarging the puncture to provide a suitable orifice through the vessel wall. The orifice and dilator tend to form a seal, preventing excess blood leakage as the dilator is advanced along and outside of the vessel. The dilator may have a pre-shaped distal end to facilitate positioning, as shown in FIG. 29c.

Figure 29D:
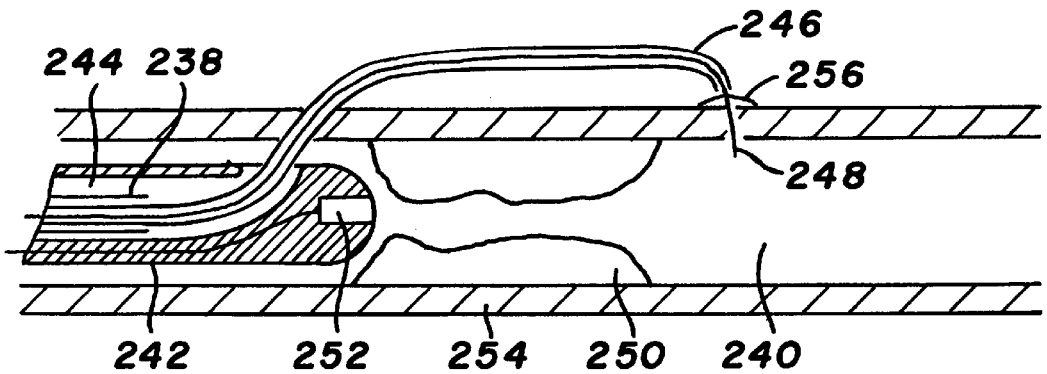
Figure 29E:
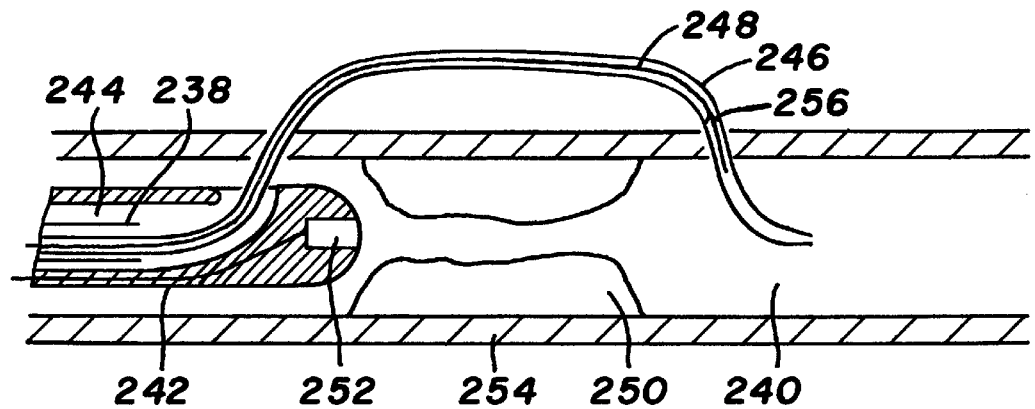

When the dilator has been advanced to a point near a selected re-entry location, needle 248 is advanced beyond the dilator to puncture vessel wall 254 (FIG. 29d). Once again, stop 256 prevents excessive needle advancement, if necessary. Alternatively the stop can limit needle travel relative to the dilator. At this point, dilator 246 is advanced over the needle (FIG. 29e), collapsing the stop and enlarging the puncture by its distal tip, entering the vessel once again. At this time, needle 248 may be completely retracted if desired.

Figure 29F:
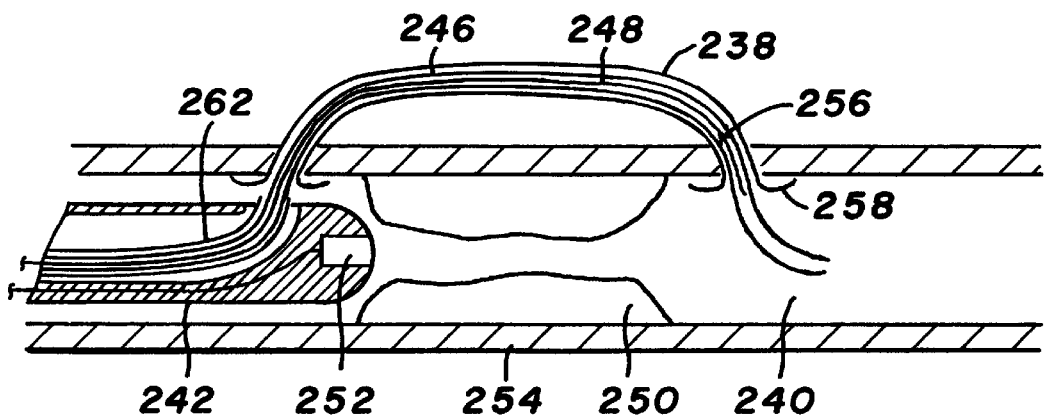
Figure 29G:
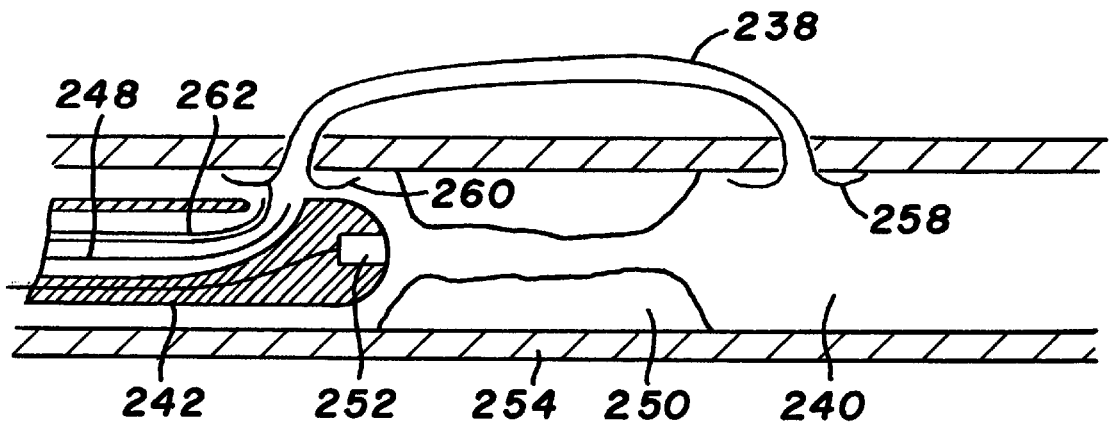
Figure 29H:
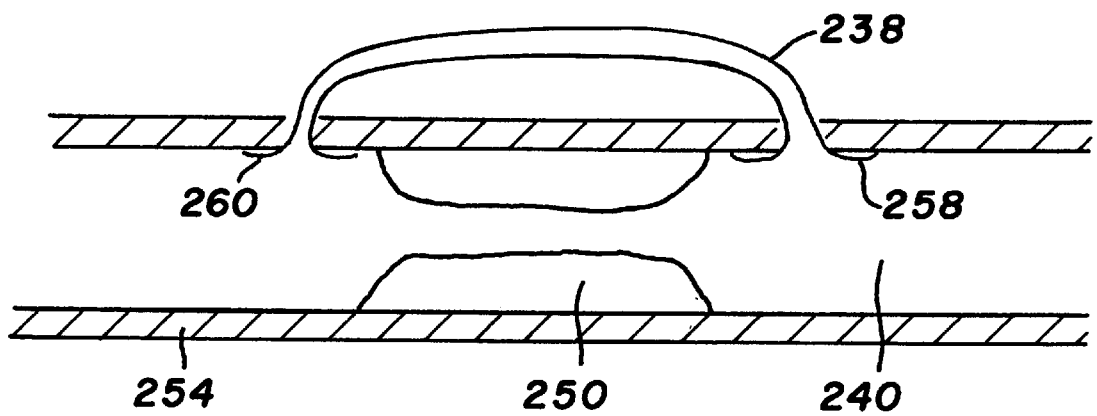

As seen in FIG. 29f, graft 238 then is advanced over dilator 246, until the graft re-enters the vessel, i.e., has its opposite ends contained, each in its respective orifice. A collet 258 at the distal end of the graft prevents graft retraction, and a collet 260 anchors the proximal end of the graft. At this point, the dilator can be retracted back into catheter 242, as shown in FIG. 29g. A hollow stylet 262 is used to advance the graft, and also to maintain the graft in place during subsequent withdrawal of the dilator. Finally, the catheter, stylet and dilator are withdrawn, leaving graft 238 secured, as seen in FIG. 29h.

Figure 30A:
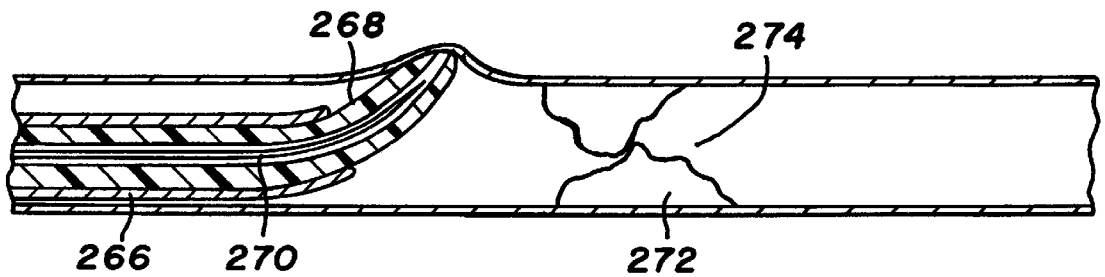

FIGS. 30a–d show an alternative system and graft deployment process, in which a graft 264 is guided to its bypass location within a catheter rather than over a dilator. The system includes a catheter 266 containing a dilator 268, which in turn contains a puncturing needle 270. These components are advanced to a position proximate a lesion 272 within a vessel 274. Dilator 268 is pre-formed with a bend at its distal region, and when positioned as shown in FIG. 30a, is directed upwardly toward the vessel wall as shown, to direct the needle toward the first intended puncture.

Figure 30B:
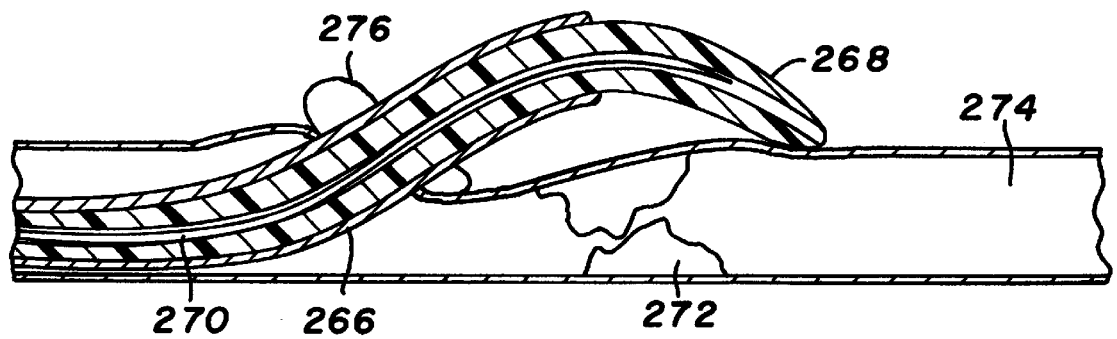

After puncture and dilation with the dilator tip, dilator 268 can be advanced over the needle, outside of and along the vessel. The dilator is rotated, preferably by the catheter using non-circular profile features as described above, to reorient the tip and point it back toward the vessel as shown in FIG. 30b. Catheter 266 is advanced along the dilator, through the orifice and outside of the vessel. A balloon 276 surrounding the catheter can be inflated at this point, to maintain the catheter against proximal withdrawal.

Figure 30C:
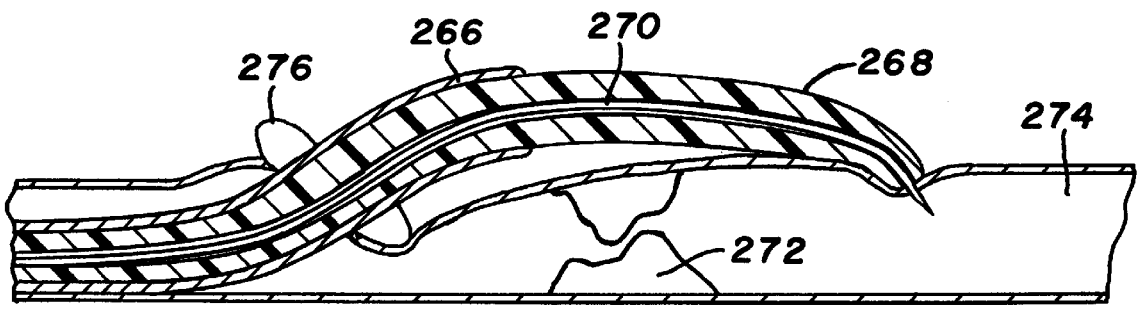

Then, with the tip of dilator 268 positioned against the vessel wall at the desired puncture location, needle 270 is advanced to form the puncture for a re-entry orifice (FIG. 30c). The dilator tip is used to enlarge the orifice, permitting advancement of the dilator into vessel 274, followed by advancement of catheter 266 over the dilator, through the orifice and into the vessel as well. Balloon 276 can be reinflated at this point, to temporarily secure the catheter.

Figure 30D:
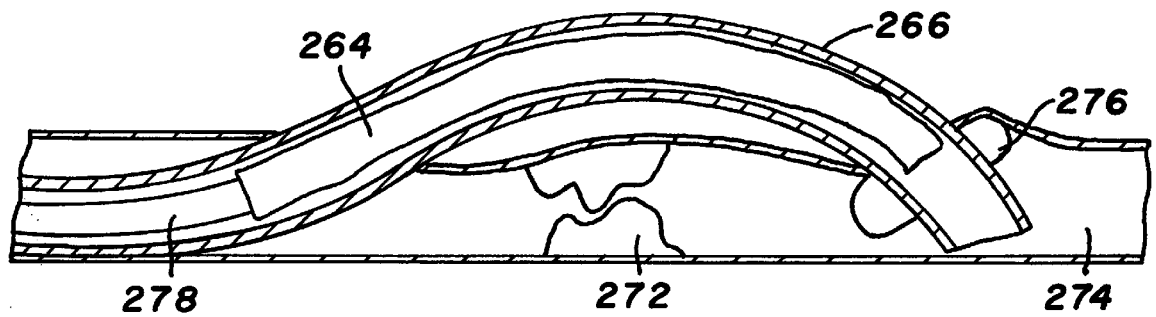

With the catheter secured, the dilator and needle are withdrawn, leaving the catheter alone as in FIG. 30d. At this stage, and after withdrawal of the dilator and needle, a graft can be inserted into the catheter and moved distally along the catheter using a stylet 278, until the graft reaches a bypass location in which each end of the graft is contained within its respective orifice. Withdrawal of the catheter (not shown), while the stylet maintains the graft in the bypass location, allows collets or other fixation mechanisms to expand and secure the graft.

This procedure is particularly suited for smaller lesions, where the dilator need travel only a short distance along the vessel.

FIGS. 31a–c illustrate a further alternative system and procedure for forming a bypass from a vessel to an organ cavity. Initially, a catheter 280 containing a dilator 282 and a needle 284 is advanced to an intended puncture site 286 within a vessel 288. The puncture is formed as previously described, and the dilator is advanced through tissue to an organ cavity 290. Then, the catheter is advanced over the dilator, becoming open to the cavity as shown in FIG. 31b. This permits use of a stylet 292 to advance a graft 294 through the catheter, until the catheter extends completely through the tissue to the cavity. Collets 293 and 295 secure the catheter. A valve 296 within the catheter limits flow to the direction indicated by the arrow. A graft 298 incorporating a valve 300 is positioned near lesion 302, to prevent backflow toward the lesion.

FIG. 32 illustrates two bypass grafts 304 and 306 used to couple the aorta to coronary vasculature in accordance with the present invention.

FIG. 33 illustrates a graft 306 collapsed around a catheter body 308, deployed in a target vessel across a stenosed lesion 310. The catheter and graft are translumenally advanced to the position shown. The opposite ends of the graft contain expandable stents 314 and 316, expanded in place with a mechanism such as those described in the aforementioned application Ser. No. 08/911,838. Alternatively, the graft ends can have self-expanding characteristics.

FIG. 34 shows the graft expanded. The ends are fully expanded into intimate contact with the vessel wall. However, along a medial region 318, graft 306 is expanded only to a nominal diameter. The diameter is selected to reduce the flow of resistance and increase cardiac output, yet prevent damage to the endothelial wall. For example, a 50% expansion usually is sufficient to open the vessel while preventing excess damage. A large space between the exterior of the graft and the vessel wall accommodates growth of the stenosed lesion, and tends to contain such growth along the vessel wall so that the vessel remains open. To accomplish this, graft 308 should have inherent radial stability, for example, by employing structural supports as previously discussed.

If desired, graft structural stability and fixation can be enhanced by forming grafts with two or more layers, with pockets formed between the layers to contain biocompatible foams which solidify when activated to provide further support. Drug solutions also can be provided in such pockets.

To improve graft radial expansion in conjunction with using the graft of FIGS. 33 and 34, channels may be formed through the lesion by cutting a slit through the vessel wall in the targeted region. A mechanical deployment system as described in the aforementioned patent application Ser. No. 08/911,838 can be used to form the required channel.

Thus, in accordance with the present invention, a more easily deployed graft is more reliably secured, to effectively bypass lesions and other blockages.

The patent applications cited herein are incorporated by reference, each in its entirety and for all purposes.

What is claimed is:

1. A body implantable graft, including:

a tubular graft wall having opposite first and second open ends, defining a fluid flow lumen between the first and second ends, adapted for a selected placement in body tissue with the first end at a first location in the tissue and the second end at a second location in the tissue, to provide a fluid flow path between the first and second locations to bypass an obstruction between the locations; and a graft fixation apparatus operable to heat the body tissue at least near the first end following said placement, to thermally secure the graft wall and the tissue adjacent the first end.

2. The graft of claim 1 wherein:

the fixation apparatus further is operable to heat the body tissue near the second end, thermally securing the graft wall and the tissue adjacent the second end.

3. The graft of claim 2 wherein:

the fixation apparatus includes a first electrically conductive heating element mounted with respect to the graft wall near first end, a second electrically conductive heating element mounted with respect to the graft wall near second end, and a means for providing an electrical current to the first and second heating elements.

4. The graft of claim 3 further including:

first and second retaining features for mechanically securing the graft wall at said first and second locations, respectively.

5. The graft of claim 1 wherein:

the graft fixation apparatus includes an electrically conductive heating element mounted with respect to the graft wall near the first end.

6. The graft of claim 5 wherein:

the heating element extends substantially the full circumferential distance around the graft wall.

7. The graft of claim 6 wherein:

the heating element is an annular member incorporating a feature for mechanically securing the first end of the graft at the first location.

8. The graft of claim 1 further including:

a valve mounted to the graft wall along the fluid flow lumen for permitting fluid flow only in one direction through the lumen.

9. The graft of claim 1 further including:

at least one pocket in the graft wall.

10. The graft of claim 5 wherein:

the means for providing electrical current to the heating element includes an RF current source, a first conductor coupled between the RF current source and the heating element, an indifferent electrode spaced apart from the heating element, and a second conductor coupled to the RF current source and to the indifferent electrode, whereby the heating of the adjacent tissue is primarily ohmic.

11. A body implantable graft, including:

a tubular graft wall having a pocket formed therein and further having opposite first and second open ends, said graft wall defining a fluid flow lumen between the first and second ends, adapted for a selected placement in body tissue with the first end at a first location in the body tissue and the second end at a second location spaced apart from the first location, to provide a fluid flow path between the first and second locations; and a graft fixation apparatus operable to heat the body tissue at least near the first end following said placement, to thermally secure the graft wall and the body tissue adjacent the first end.

12. The graft of claim 11 wherein:

the tubular graft wall is comprised of at least two layers of a graft material, and the pocket is formed between two adjacent layers.

13. The graft of claim 12 further including:

a biocompatible foam contained within the pocket.

14. The graft of claim 11 wherein:

the graft fixation apparatus includes an electrically conductive heating element mounted with respect to the graft wall near the first end.

15. The graft of claim 14 wherein:

the means for providing electrical current to the heating element includes an RF current source, a first conductor coupled between the RF current source and the heating element, an indifferent electrode spaced apart from the heating element, and a second conductor coupled to the RF current source and to the indifferent electrode, whereby the heating of the adjacent tissue is primarily ohmic.

16. The graft of claim 11 wherein:

said second location is in the body tissue, and the fixation apparatus further is operable to heat the body tissue near the second end, thermally securing the graft wall and the body tissue adjacent the second end.

17. A graft deploying system including the graft of claim 1 and further including:

an elongate and flexible carrier having a proximal end and a distal end, insertable by the distal end for intraluminal movement toward a selected site along a body lumen while the proximal end remains outside the body;

a tissue perforating mechanism proximate the distal end, positionable near the selected site and operable from the proximal end of the carrier to form a first opening through the body tissue at the first location, and further positionable near the selected site and operable to form a second opening through the body tissue at the second location;

an elongate graft guide, supported by the carrier, disposed near said distal end, and movable into a guiding position in which the graft guide extends from the first location through the first opening to the second location and through the second opening;

wherein said tubular graft wall is adapted to be mounted to the carrier for movement along the carrier; and a graft controller operable to move the tubular graft wall, when so mounted, distally along the catheter toward the graft guide, and then distally along the graft guide when the guide is in the guiding position, to a by-pass location in which the graft wall extends from the first location to the second location and further extends through the first opening and the second opening.

18. The system of claim 17 wherein:

the fixation apparatus further is operable to heat the body tissue near the second end, thermally securing the graft wall and the tissue adjacent the second end.

19. The system of claim 17 wherein:

the graft fixation apparatus includes an electrically conductive heating element mounted with respect to the graft wall near the first end.

20. The system of claim 19 wherein:

the means for providing electrical current to the heating element includes an RF current source, a first conductor coupled between the RF current source and the heating element, an indifferent electrode spaced apart from the heating element, and a second conductor coupled to the RF current source and to the indifferent electrode, whereby the heating of the adjacent tissue is primarily ohmic.

21. A body implantable graft including:

a tubular body defining a lumen and having first and second ends, adapted for placement between at least two regions of a vessel with part of the tubular body residing outside of the vessel;

at least one support structure attached to the tubular body near the first end; and a graft fixation apparatus operable to heat the vessel at least near said first end, to thermally secure the tubular body and vessel adjacent the first end.

22. The graft of claim 21 wherein:

the fixation apparatus further is operable to heat the vessel near the second end, thermally securing the tubular body and the vessel adjacent the second end.

23. The graft of claim 21 wherein:

the support structure is adapted for assuming a delivery profile to facilitate positioning the tubular body in the vessel, and further is radially expandable from the delivery profile into contact with the vessel.

24. The graft of claim 21 wherein:

the fixation apparatus includes at least one electrically conductive heating element mounted with respect to the tubular body near the first end.

25. The graft of claim 24 wherein:

the electrically conductive heating element extends substantially the full circumferential distance around the tubular body.

26. The graft of claim 24 wherein:

the electrically conductive heating element is an annular member incorporating a feature for mechanically securing the first end of the tubular body to the vessel.

27. The graft of claim 21 further including:

at least one securing feature for mechanically securing the tubular body to the vessel at least near one of the first and second ends.

28. The graft of claim 21 wherein:

the tubular body includes at least two compliant graft layers configured to form at least one pocket.

29. A thermally securable bypass graft including:

a tubular body having one end adapted for fluid coupling to the interior of a vessel with a portion of the tubular body extending outside of the vessel;

an electrode structure attached to the tubular body;

a conductor attached to the electrode structure and adapted to transmit an electrical current to the electrode structure, to heat tissue adjacent the electrode structure and thereby thermally secure the tissue to the tubular body.

30. The graft of claim 29 wherein:

the conductor is adapted for separation from the electrode structure after said thermal securing of the tubular body and tissue.

31. The graft of claim 30 wherein:

the conductor is separable from the electrode structure responsive to conducting an electrical current of sufficient amplitude to cause a breakdown of a narrowed portion of the conductor.

32. The graft of claim 29 further including:

a support structure near the electrode structure.

33. The graft of claim 32 wherein:

said support structure is adapted for assuming a delivery profile for positioning the tubular body within the vessel, and further is radially expandable into contact with the vessel after positioning.

34. The graft of claim 29 further including:

an indifferent electrode spaced apart from the electrode structure and cooperating with the electrode structure to generate an ohmic current through the tissue.

35. The graft of claim 29 wherein:

the tubular body includes at least two compliant layers that cooperate to form at least one pocket.

* * * * *